United States Patent [19]

Johnson et al.

[11] 4,119,667
[45] Oct. 10, 1978

[54] HALOANILINE DERIVATIVES AS PLANT GROWTH MODIFIERS

[75] Inventors: Wayne O. Johnson, Warminster; Harlow L. Warner, Hatboro; Roy Y. Yih, Doylestown, all of Pa.

[73] Assignee: Rohm and Haas Company, Philadelphia, Pa.

[21] Appl. No.: 526,655

[22] Filed: Nov. 25, 1974

Related U.S. Application Data

[62] Division of Ser. No. 290,190, Sep. 18, 1972, Pat. No. 3,862,833.

[51] Int. Cl.$^2$ ............................................. C07C 119/00
[52] U.S. Cl. ................................................. 260/566 F
[58] Field of Search ..................................... 260/566 F

[56] References Cited

U.S. PATENT DOCUMENTS

| | | | |
|---|---|---|---|
| 2,847,473 | 8/1958 | Robertson | 260/566 F |
| 3,279,907 | 10/1966 | Linder et al. | 71/121 |
| 3,527,594 | 9/1970 | Brepoels et al. | 71/76 |

FOREIGN PATENT DOCUMENTS 979,132  1/1965  United Kingdom ................. 260/566 F

OTHER PUBLICATIONS

Kadaba, *Journal of Pharmaceutical Sciences*, vol. 59, pp. 1190–1191 (1970).
Beran et al., C. A. vol. 43, Col. 7625–7626 (1949).
Beaver et al., J.A.C.S., vol. 79, pp. 1236–1245 (1957).
Kadaba et al., J. Heterocycl. Chem., vol. 4, pp. 301–304 (1967).

*Primary Examiner*—Gerald A. Schwartz
*Attorney, Agent, or Firm*—Bernard J. Burns

[57] ABSTRACT

This disclosure teaches that certain halo aniline derivatives, when applied post-emergence to plants, effect a modification of the growth pattern of said plant.

3 Claims, No Drawings

HALOANILINE DERIVATIVES AS PLANT GROWTH MODIFIERS

CROSS-REFERENCE TO RELATED APPLICATIONS

This is a divisional application of U.S. application Ser. No. 290,190 filed Sept. 18, 1972 now U.S. Pat. No. 3,862,833 granted Jan. 28, 1975.

SUMMARY OF THE INVENTION

The invention relates to novel and known halo aniline derivatives, to the method of using said aniline derivatives to modify plant growth, and to compositions containing said aniline derivatives as the active ingredient therein.

The regulant compositions of this invention have an active component (a) represented by compounds of the structural formulae:

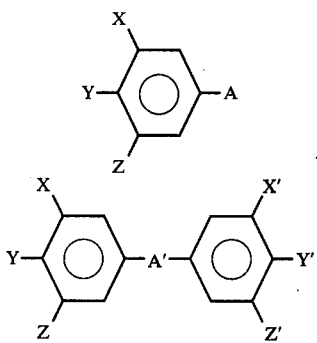

(a) wherein X and X' are selected independently from one of chlorine, bromine, and iodine; Y, Y', Z, Z' are selected independently from one of hydrogen, chlorine and bromine, provided that a single phenyl ring contains no more than two halogen atoms; A is selected independently from one of

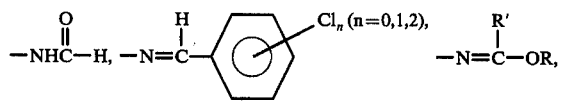

where R is lower alkyl; and R' is independently selected from one of hydrogen, methyl, or ethyl; provided when R' is methyl or ethyl, X and Z are chlorine and Y is hydrogen; A' is selected independently from one of —N=CHNH— or —NHCH$_2$NH—; provided when A' is —NHCH$_2$NH—, then Y and Y' or Z and Z' must be identical to X and X'; and (b) an inert, non-phytotoxic carrier therefor.

DESCRIPTION OF THE INVENTION

The compounds of formulae I and II are useful for control of plant growth. As such, they can be used in a variety of ways to modify and regulate plate growth patterns. The compositions of this invention can be used to increase the number of pods produced on plants. They can also be used to change other growth patterns of plants. For example, the active components of formulae I and II can be used to change the growth habit of some plants resulting in shorter and more compact plants.

The compounds of this invention are particularly effective as plant growth regulants on members of the legume family. They can be used to modify advantageously the growth pattern and thus the yield of legumes, such as the soy bean, snap bean, dry bean, lima bean, peas and others.

Limited greenhouse experiments shown that there is promotion of lateral bud growth when compounds are applied at higher concentrations and earlier timings and an increase in soybean pod numbers at lower rates applied just prior to or at the flowering stage. The preliminary biological data subsequently presented herein demonstrate this form of activity. Three parameters are reported in Table I to indicate the general spectrum of activity for each evaluated compound including the propensity for releasing lateral bud growth in soybeans. These are: (a) plant height measured as percent inhibition relative to the control; (b) the number of lateral buds per plant; and (c) phytotoxic injury on a scale of 0 to 10 (10 being maximum injury).

Preferred compounds of this invention, because of their especially beneficial plant growth regulant activity, are those compounds of formulae I and II wherein X and X' are chlorine, and either Y and Y' or Z and Z' are chlorine, while R is lower alkyl and R' is hydrogen.

The most preferred active components of this invention are:

I N,N'-Bis[3,5-dichlorophenyl]methanediamine
IV 3,5-Dichloro-N-benzylideneaniline
XIII 3,4-Dichloro-N-benzylideneaniline
XVIII 3',5'-Dichloroformanilide
XIX 3',4'-Dichloroformanilide
XX N,N'-Bis[3,5-dichlorophenyl]formamidine hydrochloride
XXI N,N'-Bis[3,4-Dichlorophenyl]formamidine hydrochloride The invention as outlined above, relates to a method of modifying plant growth which comprises applying one or more of the active components of this invention, after appropriate formulation, to the emerging plant or the locus of the plant to be treated.

One preferred aspect of this invention relates to a method for increasing harvestable pods in leguminous plants, which comprises applying an effective amount of one or more compounds disclosed herein to the growing plant.

This invention further relates to plant growth regulant compositions suitable for application to plants to modify the growth pattern of said plants, as described herein, said composition being composed of an effective amount of a compound of formulae I and II in combination with suitable non-phytotoxic adjuvants and inert carriers.

Among the active regulant compositions of the present invention are certain novel compounds in addition to previously known structures, of the following structural formulae:

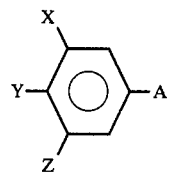

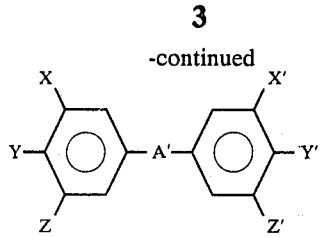

wherein X and X' are selected independently from one of chlorine, bromine, and iodine; Y, Y', Z and Z' are selected independently from one of hydrogen, chlorine and bromine, provided that a single phenyl ring contains no more than two halogen atoms; A is selected independently from one of —NHc(O)H,

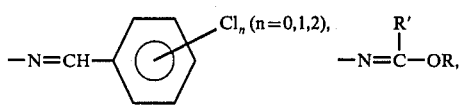

where R is lower alkyl; and R' is independently selected from one of hydrogen, methyl, or ethyl; provided when R' is methyl or ethyl, X and Z are chlorine and Y is hydrogen; and A' is selected independently from one of —N=CHNH— or —NHCH$_2$NH—, provided when A' is —NHCH$_2$HN—; then Y and Y' or Z and Z' must be identical to X and X'; and (b) an inert, non-phytotoxic carrier therefor.

Some of the more advantageous examples of novel compounds are those of one of the above formulae as follows:
I. N,N'-Bis[3,5-dichlorophenyl]methanediamine
III. N,N'-Bis[3,5-dibromophenyl]methanediamine
IV. 3,5-Dichloro-N-benzylideneaniline
XIII. 3,4-Dichloro-N-benzylideneaniline
XIV. N,N'-Bis[3,5-dichlorophenyl]formamidine Examples of specific compounds falling within formulae I and II are:
II. N,N'-Bis[3,4-dichlorophenyl]methanediamine
V. 3,5-Dichloro-N-(2-chlorobenzylidine)aniline
VI. 3,5-Dichloro-N-(3-chlorobenzylidene)aniline
VII. 3,5-Dichloro-N-(4-chlorobenzylidene)aniline
VIII. 3,5-Dichloro-N-(2,6-dichlorobenzylidene)aniline
IX. 3,4-Dichloro-N-(2-chlorobenzylidene)aniline
X. 3,4-Dichloro-N-(3-chlorobenzylidene)aniline
XI. 3,4-Dichloro-N-(4-chlorobenzylidene)aniline
XII. 3,4-Dichloro-N-(2,6-dichlorobenzylidene)aniline
XV. N,N'-Bis[3,4-dichlorophenyl]formamidine
XVI. Ethyl N-(3,5-dichlorophenyl)formimidate
XVII. Ethyl N-(3,4-dichlorophenyl)formimidate
XVIII. 3',5'-Dichloroformanilide
XIX. 3',4'-Dichloroformanilide
XX. N,N'-Bis[3,5-dichlorophenyl]formamidine HCl
XXI. N,N'-Bis[3,4-dichlorophenyl]formamidine HCl
XXII. Ethyl N-(3,5-dichlorophenyl)propionimidate Many of the dihaloaniline derivatives are compounds which are known. However, none of compounds disclosed herein, whether they be old or novel molecules, are believed to have been disclosed or suggested as having the somewhat unique utility which is first taught in the present specification.

The N-benzylideneanilines of this invention may be prepared by condensation of a 3-haloaniline, a 3,4-dihaloaniline or a 3,5-dihaloaniline with benzaldehyde or a chlorobenzaldehyde to give the respective N-benzylidene anilines:

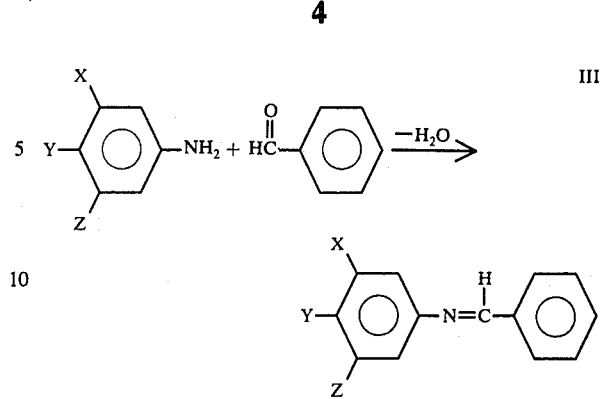

The syntheses are modeled after the preparation of N-benzylideneaniline as described by Gilman and Blatt, Organic Syntheses, Coll. Vol. I, 2nd Ed.; N.Y. - John Wiley and Sons., pps 80-81.

Novel compounds are defined by formula III above; wherein X is selected independently from chlorine, bromine, and iodine; Y and Z are selected independently from hydrogen, chlorine, and bromine provided that a single phenyl ring contains no more than two halogen atoms.

The imidates and formamidines of this invention may be prepared by condensation of a 3-haloaniline, a 3,4-dihaloaniline or a 3,5-dihaloaniline with an orthoformate ester to give an imidate. This imidate can be further reacted with another molar equivalent of the same aniline to give a symmetrically substituted formamidine or a different aniline to give an unsymmetrical formamidine, e.g.,

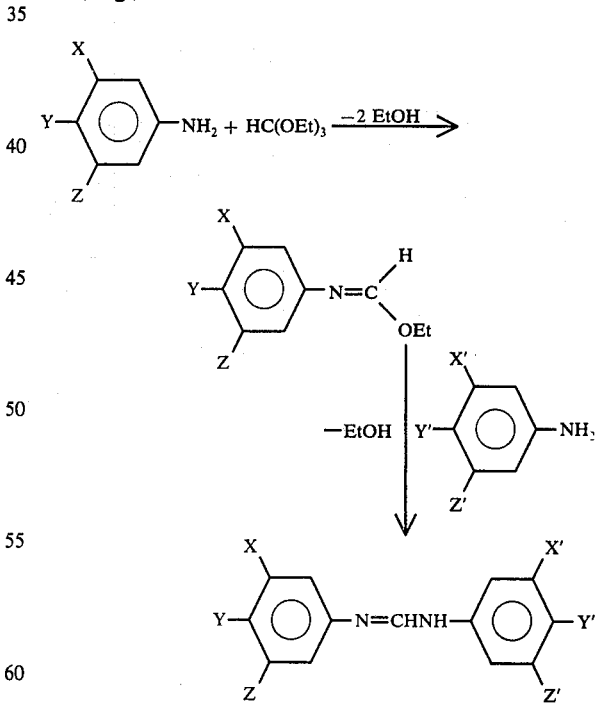

Synthetic methods are described in South African patent 68/01,921 and by Beaver et al, Journal of the American Chemical Society, 79, 1236 (1957), for the preparations of ethyl N-(3,4-dichlorophenyl)-formimidate and N,N'-bis[3,4-dichlorophenyl]formamidine, respectively.

The N,N'-bis[dihalophenyl]methanediamines of this invention may be prepared by condensation of two molar equivalents of a dihaloaniline with one molar equivalent of formaldehyde:

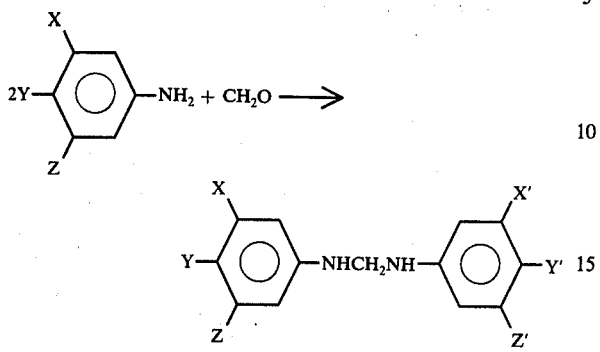

Syntheses are modeled after the preparation of N,N'-bis[3,4-dichlorophenyl]methanediamine in Belgium Pat. No. 633,272 (1963).

The formanilides of this invention may be prepared by warming the haloaniline in the presence of anhydrous formic acid, as described by N. E. Good in Plant Physiology, 36, pps. 788–803 (1961):

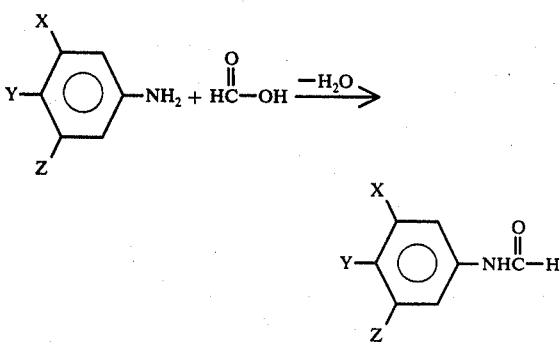

The following examples are illustrative of preparations of compounds of the invention, but are not to be construed as limitation thereof. The example numbers correspond to those given in subsequent Tables II, III, IV, V, VI, VII, presenting chemical data on exemplary compounds of this invention.

EXAMPLE I

Preparation of N,N'-Bis[3,5-dichlorophenyl]methanediamine (a) The method is modeled after the synthesis of N,N'-bis[3,4-dichlorophenyl]methanediamine (Belg. Pat. No. 633,272 and Fr. Pat. No. 1,359,549)

(b) By an alternative and more desirable method, 3,5-dichloroaniline (81 g., 0.50 mole) is dissolved in anhydrous methanol (125 ml.), of an aqueous formaldehyde solution (37%, 30 ml.) is added dropwise with stirring at room temperature over a 4½ hour period. The product is then collected by filtration (72.1 g.) ½ hour after completion of addition, m.p. 153°–6° C.

EXAMPLE IV

Preparation of 3,5-Dichloro-N-benzylidene aniline

To a reaction flask, equipped with a Dean-Stark trap, is added 3,5-dichloroaniline (16.2 g., 0.10 mole), benzaldehyde (10.6 g., 0.10 mole), p-toluenesulfonic acid monohydrate (0.2 g.), and toluene (100 ml.). The reaction mixture is then warmed to reflux and the water (1.65 ml.) collected by azeotroping. The cooled reaction mixture is treated with charcoal and the filtrate reduced in vacuo to give an amber oil, that crystallizes on standing to give 24.6 g. of product, which is recrystallized from pentane to give 18.5 g. of yellow solid, m.p. 52°–53° C.

EXAMPLE XIII

Preparation of 3,4-Dichloro-N-benzylideneaniline

Equimolar amounts of 3,4-dichloroaniline and benzaldehyde are stirred together at room temperature to give a nearly quantitative yield of product that melts at 62°–5° C. upon recrystallization from ethanol.

EXAMPLE XIV

Preparation of N,N'-Bis[3,5-dichlorophenyl]formamidine

The method of preparation is a modification of the method employed by Beaver, et al; [D. J. Beaver, D. P. Roman, and P. J. Staffel, J. Am. Chem. Soc., 79, 1236 (1957)] for the preparation of N,N'-bis[3,4-dichlorophenyl]formamidine.

3,5-Dichloroaniline (16.2 g., 0.10 mole) and triethylorthoformate (7.4 g., 0.05 mole) are charged to a flask, and a catalytic amount of p-toluenesulfonic acid monohydrate (0.30 g.) was added prior to warming to reflux. After 15 minutes at reflux a solid cake has formed. Anhydrous ethanol (10 ml.) is then added, and the reflux continued for an additional ½ hour prior to addition of toluene (15 ml.). The ethanol is then azeotroped from the reaction mixture, during which time the head temperature rises to 75° C. An additional 10 ml. of toluene is then added and heating continued until no more ethanol is collected. On cooling, the solid is collected by filtration to give 14.1 g. of product which, when recrystallized from benzene, gives a m.p. of 166°–8° C.

EXAMPLE XVI

Preparation of Ethyl N-(3,5-dichlorophenyl)formimidate

The method employed is modeled after the synthesis of ethyl N-(3,4-dichlorophenyl)formidate as described in the South African Pat. No. 68/01,921. However the acid catalyst is not employed.

3,5-Dichloroaniline (16.2 g., 0.10 mole) and triethyl orthoformate (14.8 g., 0.10 mole) are charged to flask and refluxed overnight. In the morning the condenser is replaced by a short-path distillation head and the ethanol formed is collected (8.0 ml.). A solid precipitates on cooling. This solid is collected by filtration (8.5 g.) and identified as N,N'-bis[3,5-dichlorophenyl]formamidine. The filtrate (10.6 g.) is then distilled at 0.45 mm. The fraction, b.p. 93°–98°, is collected (6.3 g.)

EXAMPLE XX

Preparation of N,N'-Bis[3,5-dichlorophenyl]formamidine hydrochloride

N,N'-Bis[3,5-dichlorophenyl]formamidine (2 g.) is dissolved in ether (50 ml) and anhydrous hydrochloric acid is bubbled through the reaction mixture to give 1.9 g. of product, which precipitated from the reaction mixture, m.p. 265°–8° C.

EXAMPLE XXII

Preparation of Ethyl N-(3,5-dichlorophenyl)propionimidate

This is prepared by the reaction of equimolar amounts of 3,5-dichloroaniline and triethyl orthopropionate, as generally described in Chemical Reviews 61, 185 (1961), to give an 86% weight yield of product distilling at 89° C./0.15 mm.

Formulation and Application

Compositions of this invention suitable for practical use as plant growth regulants will include, in addition to one or more compounds of Formulae I and II, surface active agents, solid or liquid diluents, and other materials as desired to produce wettable powders, dusts, granules or liquid concentrates.

The surface active agents used in preparing the formulations of this invention can be wetting, dispersing or emulsifying agents. They may act as wetting agents for wettable powders and dusts, as dispersing agents for emulsifiable concentrates. Surfactants may also enhance the biological activity of the substituted aniline analogs of this invention. Such surface active agents can include such anionic, cationic and nonionic agents as have heretofore been generally employed in pest control compositions of similar type.

Suitable surface active agents are set out, for example, in "Detergents and Emusifiers Annual—1967" by John W. McCutcheon, Inc. Other surface active agents not listed by McCutcheon, but still effective dispersants by virtue of protective colloid action include, methyl cellulose, polyvinyl alcohol, hydroxyethyl cellulose, and alkyl substituted polyvinyl pyrrolidines.

Suitable surface active agents for use in compositions of this invention include polyethylene glycol esters with fatty and rosin acids; polyethylene glycol ethers with alkyl phenols, or with long-chain aliphatic alcohols; polyethylene glycol ethers with sorbitan fatty acid esters; and polyoxyethylenethic ethers. Other suitable surfactants include amine, alkali and alkaline earth salts of alkylaryl sulfonic acids; amines, alkali and alkaline earth fatty alcohol sulfates; dialkyl esters of alkali metal sulfosuccinates, fatty acid esters of amine, alkali and alkaline earth isethionates and taurates; amine, alkali and alkaline earth salts of lignin sulfonic acids; methylated or hydroxyethylated cellulose; polyvinyl alcohols; alkyl substituted polyvinyl pyrrolidine; amine, alkali and alkaline earth salts of polymerized alkylnaphthane sulfonic acids; and long-chain quaternary ammonium compounds. Anionic and nonionic surface active agents are preferred.

Among preferred wetting agents are sodium alkylnaphthalene sulfonates; sodium dioctylsulfosuccinate; sodium dodecylbenzene sulfonate; ethylene oxide condensates with alkylated phenols such as octyl-, nonyl- and dodecylphenol; sodium lauryl sulfate; and trimethylnonyl polyethylene glycols.

Among preferred dispersing agents are sodium, calcium and magnesium lignin sulfonates; low-viscosity methyl cellulose; low-viscosity polyvinyl alcohol; alkylated polyvinyl pyrrolidine; polymerized alkyl naphthalene sulfonates; sodium N-oleyl or N-lauryl isethionates; sodium N-methyl-N-palmitoyl taurate, and dodecylphenol polyethylene glycol ethers.

Among preferred emulsifying agents are ethylene oxide adducts of lauric, oleic, palmitic or stearic acid esters of sorbitan or sorbitol; polyethylene glycol esters with lauric, oleic, palmitic, stearic or rosin acids, oil-soluble alkylarylsulfonates, oil-soluble polyoxyethylene ethers with octyl, nonyl and dodecylphenol, polyoxyethylene adducts to long-chain mercaptans, and mixtures of these surfactants.

Dusts

Dust compositions are those intended for application in dry form with suitable dusting equipment. Since wind drift is undesirable when applying dusts, the most suitable dust diluents are those which are dense and rapid settling. These include kaolinites, talcs, pyrophyllites, ground phosphate rock, Serecite, and ground tobacco stems. However, dusts are usually most easily prepared by diluting an existing high-strenth wettable powder with a dense diluent so that the final dust will frequently contain a fraction of light, adsorptive diluent as well as the more desirable dense filler.

A wetting agent is desirable in dust formulations so that adhesion to dew-covered foliage is enhanced. Dusts made from wettable powders will usually contain sufficient wetter, but dusts made directly from unformulated active ingredients will usually require an added wetting agent. Dry solid anionic or nonionic wetters are preferred.

Dust formulations will normally contain from 2.0 weight percent to 25 weight percent of active material, from 0.005% to 1.0% wetting agent, and from 2% to 20% light grinding aid diluent and the balance dense, rapid settling diluent. If made by diluting a prepared wettable powder, it will also contain a small amount of dispersing agent which has no active role when the composition is used as a dry dust.

Wettable Powders

These are compositions which contain inert solid diluents, in addition to surfactants, that may serve several purposes. They can act, as grinding aids to prevent mill smear and screen blinding; they can aid rapid dispersion of the mix when placed in water, they can adsorb liquid or low melting solid active material to produce a free flowing solid product, and they can permit preparation of compositions with a controlled amount of active ingredient so that proper dosage is easily measured by the consumer.

Suitable diluents can be either inorganic or organic in origin. These include the natural clays; diatomaceous earth; synthetic mineral fillers derived from silica or silicates; insoluble salts produced by precipitation in fluffy form, such as tricalcium phosphate or calcium carbonate; and powdered organic diluents such as shell, wood, or corn cob flours. Preferred fillers for the compositions of this invention include kaolin clays, attapulgite clay, nonswelling calcium magnesium montmorillonites, synthetic and magnesium silicates, sodium or calcium silica aluminates and diatomaceous silica.

Wettable powders will normally contain both a wetter and a dispersant. Most preferred for dry wettable powders are those anionic and nonionic surfactants which exist in solid form. Occasionally a liquid, nonionic surfactant, normally considered an emulsifying agent can be used to produce both wetting and dispersion.

Wetting and dispersing agents in wettable powders of this invention, when taken together, will comprise from about 0.5 weight percent to 5.0 weight percent of the total composition. The active component will be present at a concentration of from about 25% to 80% and diluent makes up the balance to 100%.

Liquid Concentrates

Liquid concentrates are formulated by combining the compounds of this invention with a suitable organic liquid. The active component may be completely dissolved in the organic liquid or it may be a finely ground suspension in a non-solvent liquid. Suitable organic liquids include alkylated naphthalenes; xylene; high molecular weight ketones, such as isophorones, dibutyl or diamyl ketone; esters such as amyl acetate; and normal or iso paraffins.

Such liquid concentrates are suitable for extension in additional organic liquids, or for dilution in water. Where the concentrate is used by extension with water, a suitable emulsifier is incorporated in the concentrate. Most preferred emulsifiers are blends of oil soluble sulfonates and nonionic polyoxyethylene glycol esters or ethers of fatty acids or alkylated phenols.

The active component in liquid concentrates will be present at from 5 weight percent to about 40 weight percent. Combined emulsifiers will be present at from 3 weight percent to about 10 weight percent and the balance will be an organic carrier liquid or solvent.

Formulations such as those described above containing as the active ingredient one or more compounds of this invention can be applied for growth regulant effect as foliar sprays.

Depending on the effect desired, the method of application and the plant treated, one or more applications may be required. The timing of the application will depend upon the plant treated. Generally, the earlier application is made to legumes at the time the first trifoliate leaf is expanding and the later applications are made from just prior to the appearance of flowers to full bloom. However, when only one application is used, it is often most advantageous to spray just prior to flower appearance.

Rates of one sixteenth to eight pounds per acre of these materials can generally be used to obtain the desired effects. For foliar application, rates of one-eighth to two pounds per acre are preferred.

The compositions of this invention for application as a spray are usually extended with water or acetone and are present in the final formulation as a solution, suspension or emulsion. The total volume of spray applied will depend on the strength of the formulation used, the plant modifying effect desired and the time of application. Generally, the volume of spray applied will be from about five to one hundred fifty gallons per acre.

The following examples will further illustrate the formulation of the compounds of this invention. Parts and percentages are by weight unless otherwise specified.

EXAMPLE A

An emulsifiable liquid of the following formulation is prepared:

|  | percent |
|---|---|
| 3,5-Dichloro-N-benzylideneaniline | 25 |
| Triton X-193* | 10 |
| Isophorone | 65 |

*An anionic surfactant comprising a blend of alkylaryl polyether alcohols and organic sulfonates supplied by Rohm and Haas Company, Philadelphia.

The above components are mixed and stirred until a homogeneous solution results and sprayed as a foliar application.

EXAMPLE B

An emulsifiable liquid of the following formulation is prepared:

|  | percent |
|---|---|
| 3,4-Dichloro-N-benzylideneaniline | 25 |
| Triton X-193 | 10 |
| Isophorone | 65 |

The above components are mixed and stirred until a homogeneous solution results, and sprayed as a foliar application.

EXAMPLE C

An emulsifiable liquid of the following formulation is prepared:

|  | percent |
|---|---|
| N,N'-Bis[3,5-dichlorophenyl]methanediamine | 5 |
| Triton X-193 | 5 |
| Isophorone | 90 |

The above components are mixed and stirred until a homogeneous solution results and sprayed as a foliar application.

EXAMPLE D

An emulsifiable liquid of the following formulation is prepared.

|  | percent |
|---|---|
| 3',5'-Dichloroformanilide | 5 |
| Triton X-193 | 5 |
| Isophorone | 90 |

The above components are mixed and stirred until a homogeneous solution results and sprayed as a foliar application.

Test Procedures

Sampling compounds were evaluated in the greenhouse in a special growth regulator test. Four to five soybean seeds (Var. Clark) were planted in 4-inch pots with a humus-soil mixture. Two weeks after planting, two uniform plants were selected from each pot for treatment. The candidate compounds were dissolved in acetone-water (1:1), and applied as a foliar spray in a carrier volume of 50 gallons per acre, using a moving belt sprayer at a rate of ¼, ½ and 2 lbs/acre. Six plants were used for each treatment. Two weeks after application, the number of laterals per plant, plant injury (0–10 scale; 0 = no effect, 10 = complete kill,) and the height of each plant were recorded. Untreated plants were used as controls. The results are set forth in Table I.

The analytical data for the exemplary compounds of the foregoing Table I are set forth subsequently in Tables II through VII.

Table I

|  | lbs./acre | No. Laterals per plant | Height (% inhib.) | Injury (0–10) |
|---|---|---|---|---|
| I | ¼ | 1 | 5 | 0 |
|  | ½ | 3 | 4 | 0 |
|  | 2 | 5 | 17 | 1 |

Table I-continued

| | lbs./acre | No. Laterals per plant | Height (% inhib.) | Injury (0–10) |
|---|---|---|---|---|
| II | 1/4 | 2 | 20 | 3 |
| | 1/2 | 0 | 15 | 2 |
| | 2 | 5 | 7 | 2 |
| III | 1/4 | 0 | 0 | 1 |
| | 1/2 | 0 | 2 | 1 |
| | 2 | 3 | 0 | 1 |
| IV | 1/4 | 3 | 7 | 0 |
| | 1/2 | 2 | 5 | 0 |
| | 2 | 5 | 17 | 1 |
| V | 1/4 | 2 | 1 | 0 |
| | 1/2 | 3 | 8 | 0 |
| | 2 | 5 | 13 | 0 |
| VI | 1/4 | 2 | 12 | 2 |
| | 1/2 | 3 | 21 | 1 |
| | 2 | 5 | 13 | 1 |
| VII | 1/4 | 2 | 3 | 0 |
| | 1/2 | 4 | 9 | 0 |
| | 2 | 5 | 13 | 0 |
| VIII | 1/4 | 0 | 1 | 0 |
| | 1/2 | 2 | 7 | 0 |
| | 2 | 5 | 15 | 0 |
| IX | 1/4 | 0 | 0 | 0 |
| | 1/2 | 4 | 23 | 0 |
| | 2 | 4 | 12 | 2 |
| X | 1/4 | 1 | 9 | 0 |
| | 1/2 | 3 | 14 | 1 |
| | 2 | 3 | 13 | 3 |
| XI | 1/4 | 1 | 4 | 0 |
| | 1/2 | 5 | 25 | 1 |
| | 2 | 4 | 14 | 3 |
| XII | 1/4 | 1 | 5 | 1 |
| | 1/2 | 2 | 15 | 1 |
| XIII | 2 | 6 | 18 | 1 |
| | 1/4 | 2 | 17 | 1 |
| | 1/2 | 4 | 9 | 0 |
| | 2 | 3 | 19 | 4 |
| XIV | 1/4 | 1 | 13 | 2 |
| | 1/2 | 3 | 11 | 3 |
| | 2 | 4 | 4 | 0 |
| XV | 1/4 | 2 | 23 | 2 |
| | 1/2 | 2 | 15 | 2 |
| | 2 | 2 | 4 | 1 |
| XVI | 1/4 | 2 | 0 | 1 |
| | 1/2 | 4 | 2 | 1 |
| | 2 | 5 | 22 | 2 |
| XVII | 1/4 | 2 | 24 | 2 |
| | 1/2 | 0 | 10 | 1 |
| | 2 | 4 | 34 | 6 |
| XVIII | 1/4 | 4 | 3 | 0 |
| | 1/2 | 5 | 11 | 1 |
| | 2 | 5 | 15 | 1 |
| XIX | 1/4 | 5 | 2 | 1 |
| | 1/2 | 0 | 0 | 0 |
| | 2 | 4 | 13 | 3 |
| XX | 1/4 | 2 | 10 | 2 |
| | 1/2 | 4 | 19 | 2 |
| | 2 | 6 | 44 | 0 |
| XXI | 1/4 | 1 | 0 | 0 |
| | 1/2 | 4 | 4 | 1 |
| | 2 | 5 | 20 | 1 |
| XXII | 1/4 | 1 | 7 | 2 |
| | 1/2 | 3 | 23 | 1 |
| | 2 | 3 | — | 1 |
| Control | | 0 | 0 | 0 |

Table II

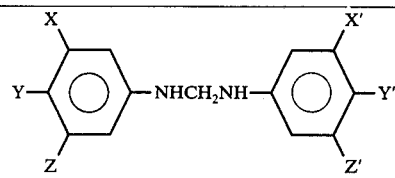

| Example | X | Y | Z | Melting Point (° C.) | Empirical Formula | Analysis Element | Found | Calculated |
|---|---|---|---|---|---|---|---|---|
| I | Cl | H | Cl | 150–51.5 | $C_{13}H_{10}Cl_4N_2$ | C | 46.50 | 46.46 |
| | | | | | | H | 3.29 | 3.00 |
| | | | | | | Cl | 42.26 | 42.20 |
| | | | | | | N | 8.26 | 8.34 |
| II | Cl | Cl | H | 110–15* | $C_{13}H_{10}Cl_4N_2$ | C | 46.62 | 46.46 |
| | | | | | | H | 2.83 | 3.00 |
| | | | | | | Cl | 41.77 | 42.20 |
| | | | | | | N | 8.15 | 8.34 |
| III | Br | H | Br | 155–9 | $C_{13}H_{10}Br_4N_2$ | C | 30.88 | 30.38 |
| | | | | | | H | 2.19 | 1.96 |
| | | | | | | Br | 62.19 | 62.20 |
| | | | | | | N | 5.40 | 5.45 |

*Lit. m.p. 124–6° C.
(Fr. 1,359,549; C.A. 61:11930b)

Table III

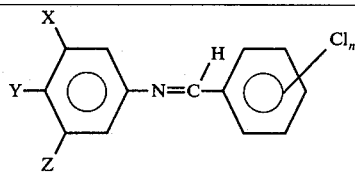

| Example | X | Y | Z | n | $Cl_n$ | Melting Point (° C.) | Empirical Formula | Analysis Element | Found | Calculated |
|---|---|---|---|---|---|---|---|---|---|---|
| IV | Cl | H | Cl | 0 | — | 52–3 | $C_{13}H_9Cl_2N$ | C | 62.56 | 62.45 |
| | | | | | | | | H | 3.62 | 3.63 |
| | | | | | | | | Cl | 28.34 | 28.32 |
| | | | | | | | | N | 5.55 | 5.60 |
| V | Cl | H | Cl | 1 | 2'-Cl | 90–91.5 | $C_{13}H_8Cl_3N$ | C | 55.13 | 54.87 |
| | | | | | | | | H | 2.72 | 2.83 |
| | | | | | | | | Cl | 37.22 | 37.38 |
| | | | | | | | | N | 4.79 | 4.92 |
| VI | Cl | H | Cl | 1 | 3'-Cl | 63–5.5 | $C_{13}H_8Cl_3N$ | C | 55.19 | 54.87 |
| | | | | | | | | H | 2.89 | 2.83 |
| | | | | | | | | Cl | 37.28 | 37.38 |

Table III-continued

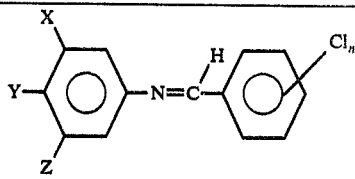

| Example | X | Y | Z | n | Cl$_n$ | Melting Point (°C.) | Empirical Formula | Element | Found | Calculated |
|---|---|---|---|---|---|---|---|---|---|---|
| VII | Cl | H | Cl | 1 | 4'-Cl | 109–10.5 | C$_{13}$H$_8$Cl$_3$N | N | 4.75 | 4.92 |
|  |  |  |  |  |  |  |  | C | 54.68 | 54.87 |
|  |  |  |  |  |  |  |  | H | 3.10 | 2.83 |
|  |  |  |  |  |  |  |  | Cl | 37.62 | 37.38 |
| VIII | Cl | H | Cl | 2 | 2',6'-Cl$_2$ | 170–2 | C$_{13}$H$_7$Cl$_4$N | N | 4.85 | 4.92 |
|  |  |  |  |  |  |  |  | C | 54.98 | 54.87 |
|  |  |  |  |  |  |  |  | H | 2.06 | 2.21 |
|  |  |  |  |  |  |  |  | Cl | 43.46 | 44.46 |
| IX | Cl | Cl | H | 1 | 2'-Cl | 88–90 | C$_{13}$H$_8$Cl$_3$N | N | 4.32 | 4.39 |
|  |  |  |  |  |  |  |  | C | 54.98 | 54.87 |
|  |  |  |  |  |  |  |  | H | 2.80 | 2.83 |
|  |  |  |  |  |  |  |  | Cl | 37.20 | 37.38 |
| X | Cl | Cl | H | 1 | 3'-Cl | 62–5 | C$_{13}$H$_8$Cl$_3$N | N | 4.85 | 4.92 |
|  |  |  |  |  |  |  |  | C | 54.85 | 54.87 |
|  |  |  |  |  |  |  |  | H | 2.73 | 2.83 |
|  |  |  |  |  |  |  |  | Cl | 37.34 | 37.38 |
| XI | Cl | Cl | H | 1 | 4'-Cl | 100–1.5 | C$_{13}$H$_8$Cl$_3$N | N | 4.78 | 4.92 |
|  |  |  |  |  |  |  |  | C | 55.18 | 54.87 |
|  |  |  |  |  |  |  |  | H | 2.82 | 2.83 |
|  |  |  |  |  |  |  |  | Cl | 37.36 | 37.38 |
| XII | Cl | Cl | H | 2 | 2,6-Cl$_2$ | 141–41.5 | C$_{13}$H$_7$Cl$_4$N | N | 4.94 | 4.92 |
|  |  |  |  |  |  |  |  | Cl | 44.29 | 44.5 |
|  |  |  |  |  |  |  |  | N | 4.07 | 4.39 |
| XIII | Cl | Cl | H | 0 | — | 62–5 | C$_{13}$H$_9$Cl$_2$N | C | 62.65 | 62.45 |
|  |  |  |  |  |  |  |  | H | 3.66 | 3.63 |
|  |  |  |  |  |  |  |  | Cl | 28.46 | 28.32 |
|  |  |  |  |  |  |  |  | N | 5.57 | 5.60 |

Table IV

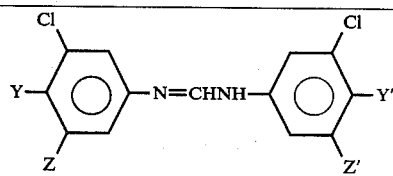

| Example | Y(Y') | Z(Z') | Melting Point (C°.) | Empirical Formula | Element | Found | Calculated |
|---|---|---|---|---|---|---|---|
| XIV | H | Cl | 166–8 | C$_{13}$H$_8$Cl$_4$N$_2$ | C | 47.0 | 46.74 |
|  |  |  |  |  | H | 2.47 | 2.41 |
|  |  |  |  |  | Cl | 42.28 | 42.46 |
|  |  |  |  |  | N | 8.32 | 8.39 |
| XV | Cl | H | 157–57.5* | C$_{13}$H$_8$Cl$_4$N$_2$ | C | 46.98 | 46.74 |
|  |  |  |  |  | H | 2.62 | 2.41 |
|  |  |  |  |  | Cl | 42.70 | 42.46 |
|  |  |  |  |  | N | 8.28 | 8.39 |

*Lit. m.p.158.3–59.1° C. [D.J.Beaver, et al., J. Am. Chem. Soc., 79, 1236 (1957)]

Table V

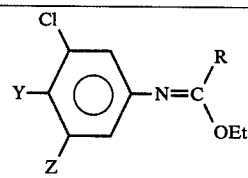

| Example | Y | Z | R | Boiling Point (°C/mm.Hg.) | Empirical Formula | Element | Found | Calculated |
|---|---|---|---|---|---|---|---|---|
| XVI | H | Cl | H | 93–8/0.45 | C$_9$H$_9$Cl$_2$NO | C | 49.70 | 49.57 |
|  |  |  |  |  |  | H | 4.43 | 4.16 |
|  |  |  |  |  |  | Cl | 31.89 | 32.52 |
|  |  |  |  |  |  | N | 6.14 | 6.42 |
| XVII | Cl | H | H | 108–8.5/0.25* | C$_9$H$_9$Cl$_2$NO |  |  |  |
| XXII | H | Cl | Et | 89/0.15 | C$_{11}$H$_{13}$Cl$_2$NO | C | 54.4 | 53.7 |
|  |  |  |  |  |  | H | 5.35 | 5.3 |
|  |  |  |  |  |  | N | 4.0 | 5.7 |

*Lit. bp 84° C./0.03 mm (S.Af. 68/01,921)

Table VI $$Y-\underset{Z}{\underset{|}{\bigcirc}}\overset{Cl}{\overset{|}{-}}-NH\overset{O}{\overset{\|}{C}}H$$

| Example | Y | Z | Melting Point (° C.) | Empirical Formula | Element | Analysis Found | Calculated |
|---|---|---|---|---|---|---|---|
| XVIII | H | Cl | 127–30* | $C_7H_5Cl_2NO$ | C | 44.18 | 44.24 |
| | | | | | H | 2.63 | 2.65 |
| | | | | | Cl | 37.14 | 37.32 |
| | | | | | N | 7.37 | 7.37 |
| XIX | Cl | H | 106–9△ | $C_7H_5Cl_2NO$ | C | 43.94 | 44.24 |
| | | | | | H | 2.64 | 2.65 |
| | | | | | Cl | 37.26 | 37.32 |
| | | | | | N | 7.29 | 7.37 |

*Lit. m.p. 127° C. [N. E. Good, Plant Physiol., 36, 788 (1961)]
△Lit. m.p. 108–9° C. [N. E. Good, Plant Physiol., 36, 788 (1961)]

Table VII $$Y-\underset{Z}{\underset{|}{\bigcirc}}\overset{Cl}{\overset{|}{-}}-N=CH-NH-\underset{Z'}{\underset{|}{\bigcirc}}\overset{Cl}{\overset{|}{-}}-Y'$$
$$HCl$$

| Example | Y | Y' | Z | Z' | Melting Point (° C.) | Empirical Formula | Element | Analysis Found | Calculated |
|---|---|---|---|---|---|---|---|---|---|
| XX | H | H | Cl | Cl | 265–8 | $C_{13}H_9Cl_5N_2$ | C | 42.12 | 42.12 |
| | | | | | | | H | 2.74 | 2.43 |
| | | | | | | | Cl | 47.92 | 47.80 |
| | | | | | | | N | 7.51 | 7.56 |
| XXI | Cl | Cl | H | H | >250 | $C_{13}H_9Cl_5N_2$ | C | 42.36 | 42.12 |
| | | | | | | | H | 2.39 | 2.43 |
| | | | | | | | Cl | 48.02 | 47.80 |
| | | | | | | | N | 7.42 | 7.56 |

A further experiment was conducted to determine the effect of selected haloaniline derivatives on soybean yields at different rates of application, and at differing stages of growth.

Procedure

Soybeans (Var. Clark) were planted at the rate of 4 seeds per 6 inch pot in a medium of 1 part humus and 2 parts soil. Two weeks after planting two uniform plants were selected from each pot for treatment. The soybeans were treated weekly with a high analysis liquid fertilizer. The candidate compounds were dissolved in acetone-water (1:1) and applied at three timings as a foliar spray in a carrier volume of 50 gallons per acre using a moving belt sprayer at rates ranging from 0.1 to two lbs. per acre. Six plants were used for each treatment. The beans were harvested eight weeks after the third treatment and the seeds and pods per plant were counted. The results are presented in Table VIII.

Compared to the control all compounds tested caused an increase in pods per plant at low rates when applied at 10% flowering or at full flowering. The increase in pods per plant resulted in an increase in seeds per plant and subsequent yield.

TABLE VIII

| | Rate lbs./A | Pods per Plant Treatment | | | Seeds per Plant Treatment | | | Seeds per Pod Treatment | | |
|---|---|---|---|---|---|---|---|---|---|---|
| | | 1st | 2nd | 3rd | 1st | 2nd | 3rd | 1st | 2nd | 3rd |
| I | 0.10 | — | 24.5 | 7.0 | — | 42.7 | 12.8 | — | 1.7 | 1.8 |
| | 0.30 | — | 14.5 | 8.3 | — | 9.3 | 13.3 | — | 0.6 | 1.6 |
| | 0.90 | — | 9.0 | 7.2 | — | 4.3 | 13.3 | — | 0.5 | 1.5 |
| XVIII | 0.10 | — | 16.2 | 9.3 | — | 17.5 | 15.2 | — | 1.1 | 1.6 |
| | 0.25 | 1.4 | — | — | 0.0 | — | — | 0.0 | — | — |
| | 0.30 | — | 9.2 | 5.2 | — | 6.3 | 10.5 | — | 0.7 | 2.0 |
| | 0.50 | 0.8 | — | — | 1.0 | — | — | 1.3 | — | — |
| | 0.90 | — | 0.5 | 5.2 | — | 0.5 | 9.5 | — | 1.0 | 1.8 |
| | 1.00 | 0.0 | — | — | 0.0 | — | — | 0.0 | — | — |
| | 2.00 | 0.0 | — | — | 0.0 | — | — | 0.0 | — | — |
| XIII | 0.10 | — | 13.7 | 5.5 | — | 20.5 | 7.8 | — | 1.5 | 1.4 |
| | 0.30 | — | 12.0 | 11.0 | — | 17.7 | 17.2 | — | 1.5 | 1.6 |
| | 0.90 | — | 5.2 | 9.3 | — | 6.7 | 16.7 | — | 1.3 | 1.8 |
| IV | 0.10 | — | 8.3 | 16.5 | — | 8.3 | 37.0 | — | 1.0 | 2.2 |
| | 0.30 | — | 0.7 | 13.2 | — | 1.0 | 23.3 | — | 1.5 | 1.7 |
| | 0.90 | — | 2.7 | 19.3 | — | 3.2 | 37.7 | — | 1.2 | 1.9 |
| Control | — | 2.1 | 5.0 | 5.0 | 4.8 | 10.0 | 10.0 | 2.2 | 2.0 | 2.0 |

We claim:
1. A compound of the formula:

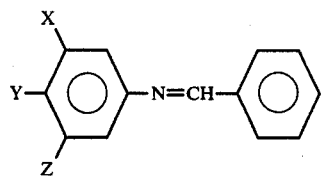
wherein X is chlorine, bromine or iodine; Y and Z are selected independently from hydrogen, chlorine and bromine; with the provision that one and only one of Y and Z is hydrogen.
2. A compound according to claim 1 wherein X and Y are chlorine and Z is hydrogen.
3. A compound according to claim 1 wherein X and Z are chlorine and Y is hydrogen.